(12) United States Patent
Luo

(10) Patent No.: US 11,135,372 B2
(45) Date of Patent: Oct. 5, 2021

(54) MEDICAL PLUNGER PUMP AND CAVITY STRUCTURE THEREOF

(71) Applicant: HUIZHOU HYDRO CARESYS MEDICAL CO., LTD., Guangdong (CN)

(72) Inventor: Fengling Luo, Guangdong (CN)

(73) Assignee: HUIZHOU HYDRO CARESYS MEDICAL CO., LTD., Huizhou (CN)

( * ) Notice: Subject to any disclaimer, the term of this patent is extended or adjusted under 35 U.S.C. 154(b) by 0 days.

(21) Appl. No.: 17/092,513

(22) Filed: Nov. 9, 2020

(65) Prior Publication Data

US 2021/0121637 A1 Apr. 29, 2021

Related U.S. Application Data

(63) Continuation of application No. PCT/CN2018/125099, filed on Dec. 28, 2018.

(30) Foreign Application Priority Data

May 10, 2018 (CN) .......................... 201810444334.6

(51) Int. Cl.
  *A61M 5/31* (2006.01)
  *A61M 5/315* (2006.01)
  *F04B 53/14* (2006.01)
  *F04B 53/16* (2006.01)

(52) U.S. Cl.
  CPC ......... *A61M 5/31513* (2013.01); *F04B 53/14* (2013.01); *F04B 53/16* (2013.01)

(58) Field of Classification Search
  CPC ...... A61M 5/31513; F04B 53/14; F04B 53/16
  See application file for complete search history.

(56) References Cited

U.S. PATENT DOCUMENTS

| 2002/0176788 | A1* | 11/2002 | Moutafis | F04B 53/143 |
|---|---|---|---|---|
| | | | | 417/415 |
| 2004/0241023 | A1* | 12/2004 | Pinkerton, III | F04B 53/162 |
| | | | | 417/461 |
| 2011/0144586 | A1* | 6/2011 | Michaud | F16J 15/56 |
| | | | | 604/151 |
| 2015/0159647 | A1 | 6/2015 | Dille et al. | |

FOREIGN PATENT DOCUMENTS

| CN | 107542638 A | 1/2018 |
|---|---|---|
| CN | 107882983 A | 4/2018 |
| CN | 108397381 A | 8/2018 |
| CN | 208416912 U | 1/2019 |
| EP | 2434140 A1 | 3/2012 |
| JP | 2008164097 A | 7/2008 |

\* cited by examiner

*Primary Examiner* — Amber R Stiles

(57) ABSTRACT

A medical plunger pump and a chamber structure thereof. The chamber structure includes a barrel, where the barrel is provided with at least one cylindrical chamber which includes a piston working section in which a piston is able to reciprocate and a joint section where the piston is connected to a push rod. The joint section includes a first arc section that protrudes from the piston working section, where a first end of the first arc section is smoothly connected to a side wall of the piston working section, and a second end of the first arc section is bent and extendable along an axis of the piston working section. The medical plunger pump includes the above-mentioned chamber structure.

14 Claims, 5 Drawing Sheets

MEDICAL PLUNGER PUMP AND CAVITY STRUCTURE THEREOF

CROSS-REFERENCE TO RELATED APPLICATIONS

This application is a continuation of International Patent Application No. PCT/CN2018/125099 with a filing date of Dec. 28, 2018, which claims the benefit of priority from Chinese Patent Application No. 201810444334.6 with a filing date of May 10, 2018. The content of the aforementioned applications, including any intervening amendments thereto, is incorporated herein by reference.

TECHNICAL FIELD

The present application relates to medical pumps, and more particularly to a medical plunger pump and a chamber structure thereof.

BACKGROUND

In fluid power technology, a high-pressure pump is one of core components of a medical fluid power system, and generally adopts a plunger pump that is widely used as a standard part. In the existing medical high-pressure pumps, a cylindrical chamber is generally provided with an inlet channel and a water outlet channel. When a liquid enters the plunger pump for pressurization, a continuous flow of high-pressure water is pumped out through the reciprocating movement of the piston.

Commonly, the piston is fixedly connected to the push rod, and the piston is generally designed for a single use to meet the high sanitation requirements of medical pumps, as a result, the push rod has to be discarded together with the piston. For cost saving, it is better to detachably connect the piston and the push rod, however, this could lead to increased process complexity and inconvenience in use. Besides, the cylindrical chamber of the existing plunger pumps generally has an inner wall with a constant diameter and an inclined section, and a sharp point is formed at a junction of the inner wall and the inclined section. When the piston is pushed into the cylindrical chamber, an outer surface of the piston is easy to be scratched by the sharp point, resulting in an increase in the roughness of the outer surface of the piston. However, the rough outer surface of the piston can easily destroy the mirror surface of the cylindrical chamber, which not only affects the sealing effect, but also reduces the service life of the chamber structure. Moreover, due to gentle variation of the inner diameter of cylindrical chamber resulted from the slope of the inclined section, the inclined section becomes longer, which lengthens and enlarges the cylindrical chamber.

SUMMARY

An object of the disclosure is to provide a plunger pump and a chamber structure thereof which is beneficial to reduce the damage of the chamber structure, improve the service life of the chamber structure, and at the same time facilitate a stable connection between the piston and the push rod.

The technical solutions of the disclosure are described as follows.

In a first aspect, the present disclosure provides a chamber structure of a medical plunger pump, comprising:
a barrel;
wherein the barrel is provided with at least one cylindrical chamber; the at least one cylindrical chamber comprises a piston working section in which a piston is able to reciprocate and a joint section where the piston is connected to a push rod; the joint section comprises a first arc section that protrudes from the piston working section, wherein a first end of the first arc section is smoothly connected to a side wall of the piston working section, and a second end of the first arc section is bent and extendable along an axis of the piston working section.

In an embodiment, a bend radius of the first arc section is 1 mm-30 mm.

In an embodiment, a surface roughness of an inner wall of the piston working section is Ra0.012-Ra1.6 or Rmax0.4-Rmax64 or Rz0.025-Rz1.6, where Ra refers to Roughness Average which is the arithmetic average of the absolute values of the profile height deviations from the mean line, recorded within the evaluation length; Rmax refers to Maximum Roughness Depth which is the largest single roughness depth within the evaluation length; and Rz refers to Mean Roughness Depth which is the arithmetic mean value of the single roughness depths of consecutive sampling lengths.

In an embodiment, the at least one cylindrical chamber further comprises a turbulent flow section; the turbulent flow section is provided with a curved wall which is recessed in a direction away from the piston working section, and the curved wall is connected to the side wall of the piston working section.

In an embodiment, the barrel is further provided with an outlet channel and an inlet channel which are in communication with the at least one cylindrical chamber; and axes of the outlet channel and the inlet channel offset from the axis of the piston working section.

In an embodiment, a distance between an axis of the outlet channel and the axis of the piston working section is 0.1 mm-50 mm; a distance between an axis of the inlet channel and the axis of the piston working section is 0.1 mm-50 mm; and two ends of the outlet channel and two ends of the inlet channel are respectively provided with a fillet having a radius of 0.05 mm-1.5 mm.

In an embodiment, the curved wall and the side wall of the piston working section are connected by a tool withdrawal groove, and a width of the tool withdrawal groove is 0.1 mm-10 mm.

In an embodiment, the at least one cylindrical chamber further comprises a clearance section with an inner diameter larger than that of the piston working section; the clearance section is connected to the second end of the first arc section; a side wall of the clearance section is provided with an annular groove; and a blocking piece is embedded in the annular groove.

In an embodiment, the at least one cylindrical chamber further comprises a guide section, and one end of a side wall of the guide section is connected to the joint section.

In an embodiment, the guide section comprises a linear section and a second arc section; two ends of the second arc section are respectively connected to the linear section and the second end of the first arc section; the linear section is parallel to the axis of the piston working section; a first end of the second arc section is tangent to the second end of the first arc section; and a second end of the second arc section is tangent to the linear section.

In an embodiment, the guide section comprises an inclined section, a third arc section, and a linear section; the second end of the first arc section, the inclined section, the third arc section and the linear section are connected in sequence; the linear section is parallel to the axis of the piston working section; the first arc section is tangent to the inclined section; the inclined section is tangent to the third arc section; and the third arc section is tangent to the linear section.

In an embodiment, the at least one cylindrical chamber further comprises a clearance section with an inner diameter larger than that of the piston working section; two ends of the guide section are respectively connected to the joint section and the clearance section; the side wall of the clearance section is provided with an annular groove; and a blocking piece is embedded in the annular groove.

In an embodiment, the at least one cylindrical chamber consists of at least two cylindrical chambers.

In a second aspect, the present disclosure provides a medical plunger pump, comprising the mentioned chamber structure, wherein a piston assembly is slidably provided in the cylindrical chamber; the piston assembly comprises the push rod and a piston; and the piston comprises a sealing portion tightly attached to a side wall of the piston working section and a joint portion that is able to engage with the push rod in the joint section.

In an embodiment, the joint portion comprises at least two claws; one end of each of the at least two claws is connected to the sealing portion, and the other end of each of the at least two claws is extendable in a direction deviating from an axis of the sealing portion; and a clamping cavity is formed after the at least two claws are closed; and a clamping portion is provided at one end of the push rod to cooperate with the at least two claws in the joint section in a snap fit.

Compared to the prior art, the present invention has following beneficial effects.

The chamber structure of the present application has a simple structure. When the push rod pushes the piston to move in the joint section, the piston engages with the push rod under the squeezing action of the first arc section. At the same time, the arrangement of the first arc section enables smooth contact between the piston and the cylindrical chamber when the piston assembly enters the piston working section, thereby reducing the friction between the piston and the inner wall of the cylindrical chamber, so that the movement of the piston in the cylindrical chamber is softer, and the piston can be pushed into the cylindrical chamber with a relatively smaller pushing force. In addition, the junction between the first arc section and the side wall of the piston working section is relatively smooth, which can further reduce the drastic changes in stress and reduce the risk of damage to the outer surface of the piston without damaging the roughness of the outer surface of the piston, so as not to destroy the mirror effect of the cylindrical chamber, thereby maintaining the high pressure of the chamber structure and prolonging the service life of the chamber structure. Finally, the change of the first arc section is greater than that of the inclined section, which can shorten the distance from the open end of the cylindrical chamber to the piston working section, thereby reducing the volume of the chamber structure.

In the present invention, the push rod is close to the piston, and then pushes the piston into the cylindrical chamber. During which, the clamping cavity is gradually closed under the action of the first arc section, and is connected to the clamping part of the push rod in a snap fit, thereby fixing the piston and the push rod in an easy and convenient manner, where the push rod can be pushed into the cylindrical chamber and the piston can be connected to the push rod without any additional action.

Figure 1:
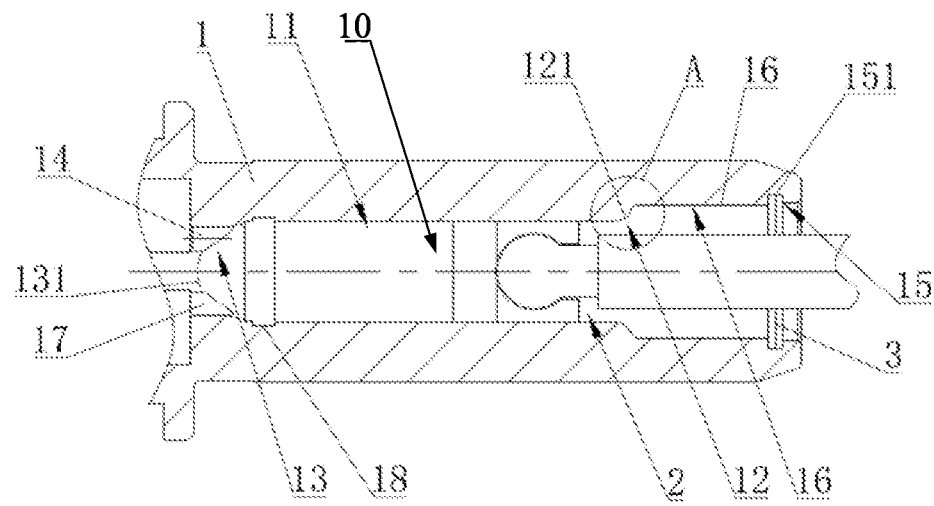
FIG. 1 is a schematic diagram showing the engagement of a push rod and a piston according to Embodiment 1 of the present disclosure.

In the drawings:
1, barrel;
10, cylindrical chamber;
11, piston working section;
12, joint section;
121, first arc section;
13, turbulent flow section;
131, curved wall;
14, outlet channel;
15, clearance section;
151, annular groove;
16, guide section;
161, linear section;
162, second arc section;
163, inclined section;
164, third arc section;
17, inlet channel;
18, tool withdrawal groove;
2, piston assembly;
21, piston;
211, sealing portion;
212, joint portion;
2121, claw;
2122, clamping cavity;
22, push rod;
221, clamping portion; and
3, blocking piece.

DETAILED DESCRIPTION OF EMBODIMENTS

The present disclosure will be further described in detail below with reference to the accompanying drawings and the embodiments. The embodiments disclosed in the present disclosure are only illustrative, but not intended to limit the scope of the present disclosure.

Embodiment 1

Referring to FIGS. 1-5 and 8, a chamber structure of a medical plunger pump, includes a barrel 1, where the barrel 1 is provided with at least one cylindrical chamber. The at least one cylindrical chamber includes a piston working section 11 in which a piston 21 is able to reciprocate and a joint section 12 where the piston 21 is connected to a push rod 22. The joint section 12 includes a first arc section 121 that protrudes from the piston working section 11, where a first end of the first arc section 121 is smoothly connected to a side wall of the piston working section 11, and a second end of the first arc section 121 is bent and extendable along an axis of the piston working section 11.

In the present application, the chamber structure has a simple structure. When the push rod 22 pushes the piston 21 to move in the joint section 12, the piston 21 engages with the push rod 22 under the squeezing action of the first arc section 121. At the same time, the arrangement of the first arc section reduces contact area between the piston 21 and the cylindrical chamber 10 when the piston assembly 2 enters the piston working section 11, thereby reducing the friction between the piston 21 and the inner wall of the cylindrical chamber 10, so that the movement of the piston 21 in the cylindrical chamber 10 is softer, and the piston 21 can be pushed into the cylindrical chamber with a relatively smaller pushing force. In addition, the junction between the first arc section 121 and the side wall of the piston working section 11 is relatively smooth, which can further reduce the drastic changes in stress and reduce the risk of damage to the outer surface of the piston 21 without damaging the roughness of the outer surface of the piston 21, so as not to destroy the mirror effect of the cylindrical chamber, thereby effectively sealing the cylindrical chamber 10 and prolonging the service life of the cylindrical chamber 10. Finally, the change of the first arc section 121 is greater than that of the inclined section, which can shorten the distance from the open end of the cylindrical chamber to the piston working section 11, thereby shortening a length of the cylindrical chamber 10 and thus reducing the volume of the cylindrical chamber 10.

In the present embodiment, a bend radius of the first arc section 121 is 1 mm-30 mm, so that the first arc section has gentle path variation, which further reduces the friction between the piston and the cylindrical chamber 10 during the movement of the piston in the piston working section, and prolongs the service life of the cylindrical chamber 10.

Specifically, a surface roughness of an inner wall of the piston working section 11 is Ra0.012-Ra1.6 or Rmax0.4-Rmax64 or Rz0.025-Rz1.6. In this way, the piston 21 can move within the piston working section 11 with high moving efficiency and good sealing effect, at the same time, fluid can flow in the piston working section 11 with less friction between the fluid and an inner wall surface of the piston working section 11, thereby reducing heat generated by friction to benefit the working environment. Moreover, the inner wall of the piston working section 11 with the above roughness can not only have good working characteristics, but also help control the processing cost, and improve the yield and quality of the product.

The at least one cylindrical chamber 10 further includes a turbulent flow section 13. The turbulent flow section 13 is provided with a curved wall 131 which is recessed from the piston working section 11, and the curved wall 131 is connected to the side wall of the piston working section 11. The cylindrical chamber 10 is further provided with an outlet channel 14 and an inlet channel 17. The outlet channel 14 is in communication with the at least one cylindrical chamber, and an axis of the outlet channel 14 offsets from the axis of the piston working section. The inlet channel 17 is in communication with the at least one cylindrical chamber, and an axis of the inlet channel offsets from the axis of the piston working section 11. The curved wall 131 is configured to slow down the impact of the fluid hitting a bottom of the cylindrical chamber. At the same time, the outlet channel 14 offsets from the axis of the piston working section 11 and is communicated with the curved wall 131, so that after the fluid impacts the curved wall 131, a turbulent flow is formed and flows out from a side of the curved wall 131, instead of being directly squeezed out from the outlet channel 14 by the piston 21, which is beneficial to increasing the pressure of the fluid that is pumped out of the chamber structure through the outlet channel 14, thereby forming a high-pressure fluid.

Further, a distance between an axis of the outlet channel 14 and the axis of the piston working section 11 is 0.1 mm-50 mm, and a distance between an axis of the inlet channel 17 and the axis of the piston working section is 0.1 mm-50 mm, so as to reduce a size of an interior of the cylindrical chamber 10. Two ends of the outlet channel 14 and two ends of the inlet channel 17 are respectively provided with a fillet having a radius of 0.05 mm-1.5 mm, so as to reduce burrs formed during processing the outlet channel 14 and the inlet channel 17, allowing for the fluid to smoothly flow in the outlet channel 14 and the inlet channel 17 and reducing hydraulic loss when the fluid flows.

In the present embodiment, the curved wall 131 and the side wall of the piston working section 11 are connected by a tool withdrawal groove 18, so that during the process of grinding the inner wall of the cylindrical chamber 10, the tool is able to extend its machining surface to an end of the piston working section 11. A width of the tool withdrawal groove 18 is 0.1 mm-10 mm, which is convenient for the subsequent withdrawal of the tool.

Specifically, the at least one cylindrical chamber further includes a guide section 16. One end of a side wall of the guide section 16 is connected to the joint section 12. In the present embodiment, the guide section 16 includes a linear section 161 and a second arc section 162. A second end of the second arc section 162 is connected to the linear section 161. A first end of the second arc section 162 is connected to the second end of the first arc section 121. An axis of the linear section 161 is parallel to the axis of the piston working section 11; the first end of the second arc section 162 is tangent to the second end of the first arc section 121; and the second end of the second arc section 162 is tangent to the linear section 161. Based on the above-mentioned structure, the piston 21 is pushed in the linear section 161 and the second arc section 162 in sequence to make it easier for the piston 21 to enter the joint section 12, and then the piston 21 and the push rod 22 are fixedly connected in the joint section 12, so as to further improve efficiency of connecting them. In practical applications, a diameter of the second arc section 162 can be modified as needed.

Referring to FIG. 1, the at least one cylindrical chamber 10 further includes a clearance section 15 with an inner diameter larger than that of the piston working section 11. Two ends of the guide section 16 are respectively connected to the joint section 12 and the clearance section 15. A side wall of the clearance section 15 is provided with a annular groove 151, and a blocking piece 3 is embedded in the annular groove 151 to prevent the piston 21 from exiting the cylindrical chamber under the action of the push rod 22, so that a liquid does not flow out of the cylindrical chamber to cause pollution.

Figure 2:
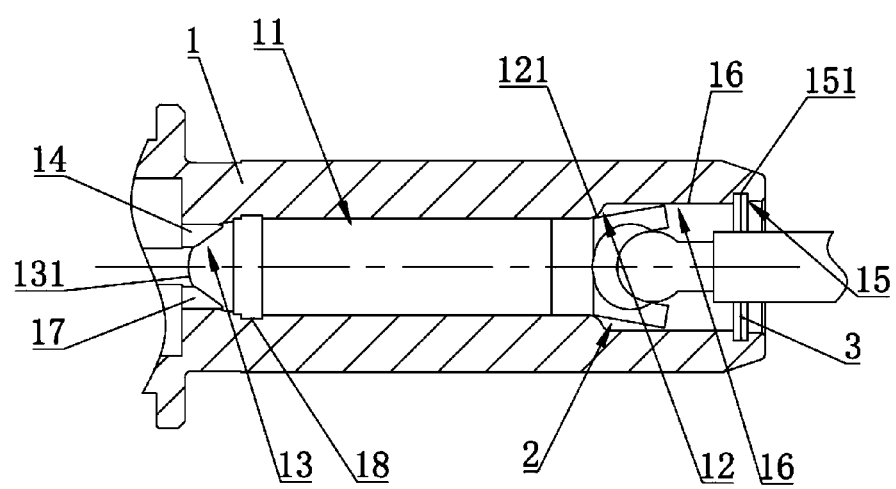
FIG. 2 is a schematic diagram showing the disengagement of the push rod and the piston according to Embodiment 1 of the present disclosure.
Figure 3:
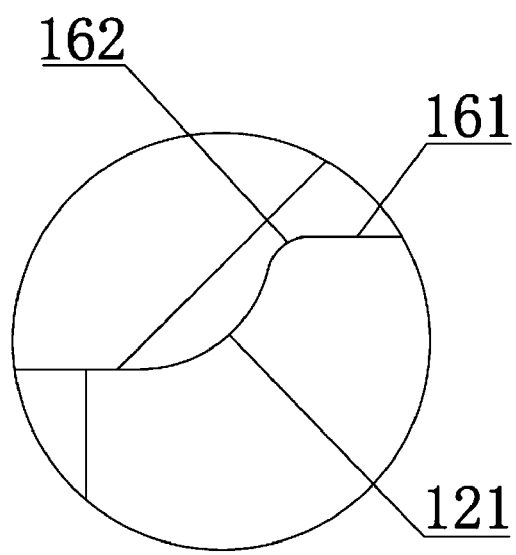
FIG. 3 is an enlarged view of Detail A according to Embodiment 1 of the present disclosure.
Figure 4:
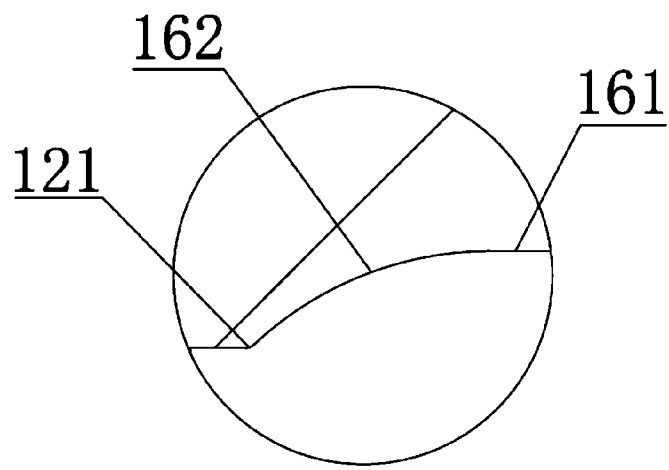
FIG. 4 is an enlarged view of Detail A according to Embodiment 1 of the present disclosure, where a diameter of the second arc section is different from that in FIG. 3.
Figure 5:
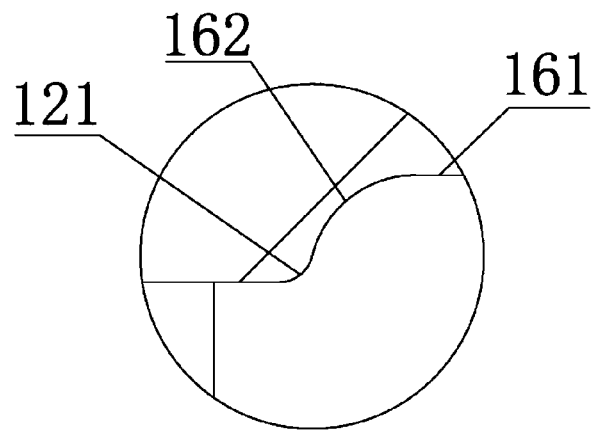
FIG. 5 is an enlarged view of Detail A according to Embodiment 1 of the present disclosure, where the diameter of the second arc section is different from that in FIG. 3 and FIG. 4.
Figure 8:
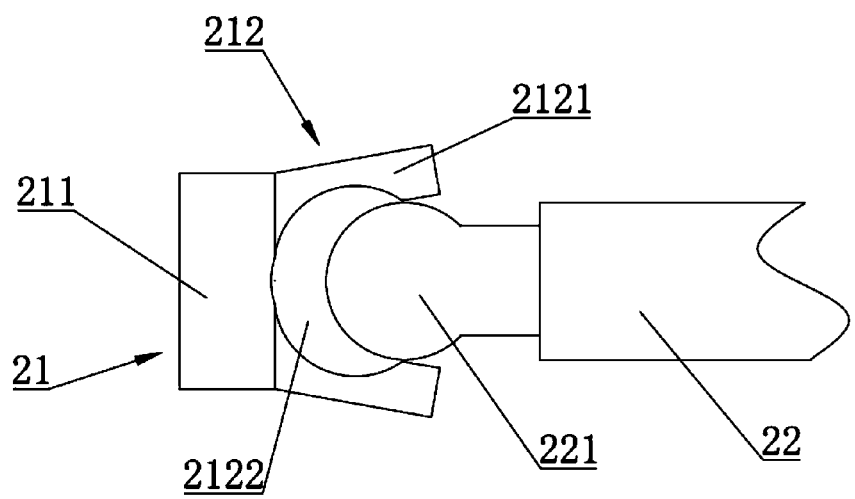
FIG. 8 is a schematic diagram of a piston assembly according to Embodiments 1-4 of the present disclosure.

Referring to FIGS. 1-2 and 8, a medical plunger pump includes the above-mentioned cylindrical chamber, where a piston assembly 2 is slidably provided in the cylindrical chamber 10. The piston assembly 2 includes a piston 21 and a push rod 22, and the piston 21 includes a sealing portion 211 tightly attached to a side wall of the piston working section 11 and a joint portion 212 that is able to engage with the push rod 22 in the joint section. The joint portion 212 includes at least two claws 2121. One end of each claw 2121 is connected to the sealing portion 211, and the other end of each claw 2121 is extendable in a direction deviating from an axis of the sealing portion 211. Ends of each claw 2121 away from the sealing portion 211 extend inward to form a clamping cavity 2122. A clamping portion 221 is provided at one end of the push rod 22 to cooperate with the at least two claws in the joint section 12 in a snap fit. During use, the push rod 22 moves toward the piston 21 to touch and then push the piston 21 into the cylindrical chamber 10. During which, an angle of 1°-45° is firstly formed between each claw 2121 and the axis of the piston 21, next, the push rod 22 is continue to be pushed, so that the at least two claws 2121 gradually move along the first arc section 121 toward the piston working section 11. In this process, the angle formed by each claw 2121 and the axis of the piston 21 is gradually reduced, so that the at least two claws 2121 are gradually closed, and finally, the at least two claws 2121 are closed to form a clamping cavity 2122 to engage with the clamping portion 221 at one end of the push rod 22, thereby realizing that the push rod 22 drives the piston 21 to reciprocate in the piston working section 11.

Specifically, the clamping portion 221 may be, but is not limited to, a cylindrical boss or a spherical back cone, and may be any structure that can connect two parts and prevent their separation. At the same time, a shape of the clamping cavity 2122 matches a shape of the clamping portion 221, so that the at least two claws 2121 can engage better with the clamping part 221 in a snap fit.

The at least two claws 2121 are gradually closed to form the clamping cavity 2122 under the action of the first arc section 121. During which, the clamping part 221 is accommodated in the clamping cavity 2122 such that the at least two claws 2121 engage with the clamping part 221 in a snap fit, thereby fixing the piston 21 and the push rod 22 in an easy and convenient manner, where the push rod 22 can be pushed into the cylindrical chamber 10 and the piston 21 can be connected to the push rod 22 without any additional action.

Embodiment 2

Figure 6:
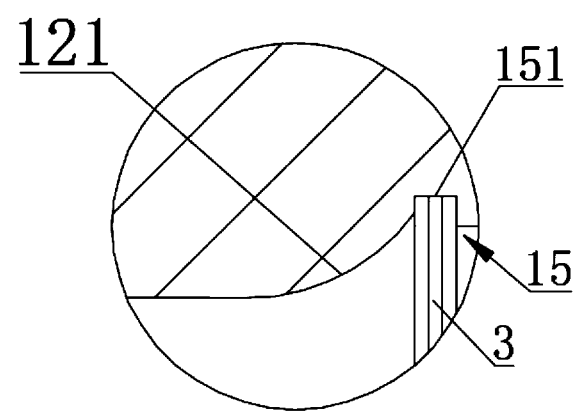
FIG. 6 is an enlarged view of a junction between a joint section and a clearance section according to Embodiment 2 of the present disclosure.

Referring to FIG. 6, this embodiment differs from Embodiment 1 in that there is no guide section 16 between the joint section 12 and the clearance section 15, and the second end of the joint section 12 is connected to the clearance section 15, thereby reducing a distance between the piston working section 11 and an open end of the cylindrical chamber, so that in a cylindrical chamber 10 of the same size, the piston 21 moves more smoothly under the action of the push rod 22, thereby reducing the risk of damage to surfaces of the piston 21.

The other structures of this embodiment are the same as that of Embodiment 1, which will not be repeated herein.

Embodiment 3

Figure 7:
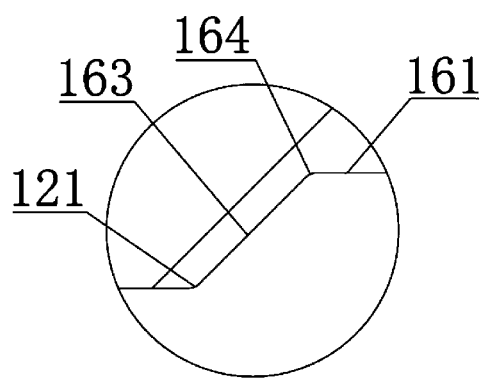
FIG. 7 is an enlarged view of a junction between the joint section and a guide section according to Embodiment 3 of the present disclosure.

Referring to FIG. 7, this embodiment differs from Embodiment 1 in that the guide section 16 includes an inclined section 163, a third arc section 164, and a linear section 161. An axis of the linear section 161 is parallel to an axis of the piston working section 11. The second end of the first arc section 121, the inclined section 163, and the third arc section 164 and the linear section 161 are connected in sequence. The first arc section 121 is tangent to the inclined section 163. The inclined section 163 is tangent to the third arc section 164. The third arc section 164 is tangent to the linear section 161. Based on the above-mentioned structure, the piston is pushed along the linear section 161, the third arc section 164 and the inclined section 163 in sequence, so that the piston 21 can easily enter the joint section 12, and then the piston 21 and the push rod 22 are fixedly connected in the joint section 12, which further improves the efficiency of connecting them.

The other structures of this embodiment are the same as that of Embodiment 1, which will not be repeated herein.

Embodiment 4

Figure 9:
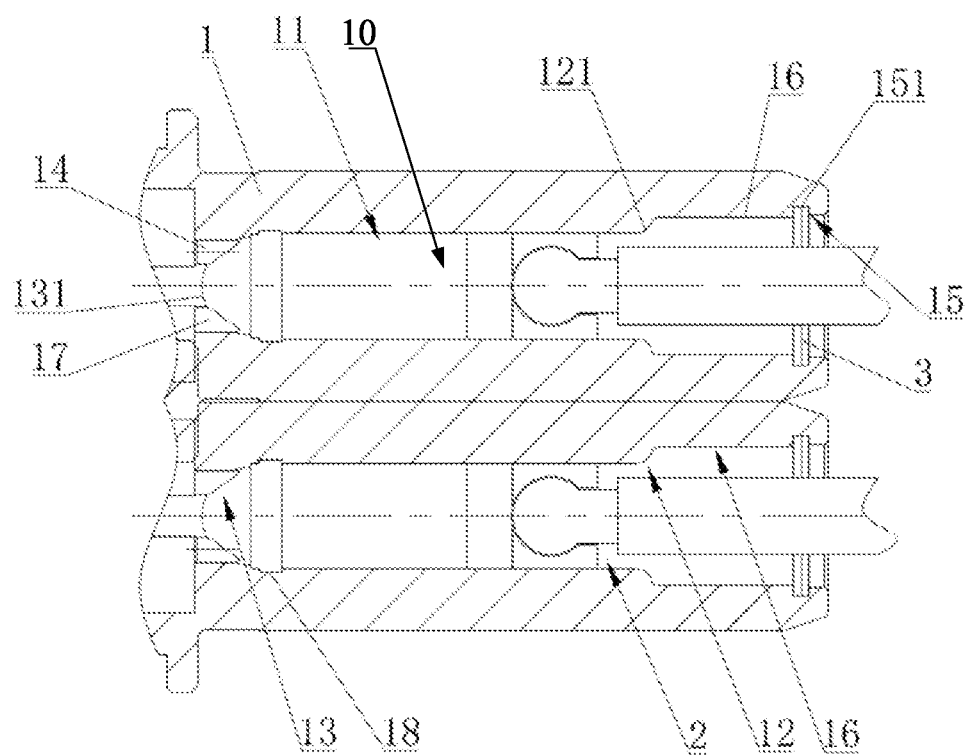
FIG. 9 is a schematic diagram showing the engagement of the push rod and the piston according to Embodiment 4 of the present disclosure.

Referring to FIG. 9, this embodiment differs from Embodiment 1 in that at least two cylindrical chambers 10 and at least two pistons 21 are provided. There is a one-to-one match between the at least two cylindrical chambers 10 and the at least two pistons 21. For example, the at least two cylindrical chambers 10 consist of two cylindrical chambers 10, and the at least two pistons 21 consist of two pistons 21, and there is a one-to-one match between the two cylindrical chambers 10 and the two pistons 21. The two pistons 21 alternately reciprocate in the two cylindrical chambers 10 respectively, so fluid can always be stably pumped out of the cylindrical chambers, which is different from a single cylindrical chamber. When the fluid is pumped into a single cylindrical chamber, there is no continuous flow of water pumped out from the outlet channel 14, that is, the single cylindrical chamber involves poor stability of water flow output. Therefore, this embodiment improves the stability of water flow pumped out of the cylindrical chamber.

The other structures of this embodiment are the same as that of Embodiment 1, which will not be repeated herein.

In summary, the first arc section 121 is provided in all embodiments in the present disclosure. When the push rod 22 pushes the piston 21 to move in the joint section 12, the piston 21 engages with the push rod 22 under the squeezing action of the first arc section 121. At the same time, the arrangement of the first arc section reduces contact area between the piston and the cylindrical chamber when the piston assembly 2 enters the piston working section 11, thereby reducing the friction between the piston 21 and the inner wall of the cylindrical chamber, so that the movement of the piston 21 in the cylindrical chamber is softer, and the piston 21 can be pushed into the cylindrical chamber with a relatively smaller pushing force. In addition, the junction between the first arc section 121 and the side wall of the piston working section 11 is relatively smooth, which can further reduce the drastic changes in stress and reduce the risk of damage to the outer surface of the piston 21 without damaging the roughness of the outer surface of the piston 21, so as not to destroy the mirror effect of the cylindrical chamber, thereby effectively sealing the cylindrical chamber 10 and prolonging the service life of the cylindrical chamber 10. Finally, the change of the first arc section 121 is greater than that of the inclined section, which can shorten the distance from the open end of the cylindrical chamber to the piston working section 11, thereby reducing the volume of the cylindrical chamber 10.

It should be understood that the terms "first", "second" and the like used herein are for the purpose of illustration of elements which are not limited thereto. These terms are only used to distinguish the same type of elements from each other. For example, without departing from the scope of the present disclosure, a "first" element refers to a "second" element, and similarly, a "second" element can refer to a "first" element.

Described above are only preferred embodiments of the present disclosure, which are not intended to limit the present invention. It should be noted that all equivalent changes made by those skilled in the art without departing from the spirit of the present disclosure shall fall within the scope of the disclosure defined by the appended claims.

What is claimed is:

1. A chamber structure of a medical plunger pump, comprising: a barrel;
   wherein the barrel is provided with at least one cylindrical chamber; the at least one cylindrical chamber comprises a piston working section in which a piston is able to reciprocate and a joint section where the piston is connected to a push rod; the joint section comprises a first arc section that protrudes from the piston working section, wherein a first end of the first arc section is smoothly connected to a side wall of the piston working section, and a second end of the first arc section is bent and extendable along an axis of the piston working section, wherein a bend radius of the first arc section is 1 mm-30 mm.

2. The chamber structure of claim 1, wherein a surface roughness of an inner wall of the piston working section is Ra0.012-Ra1.6 or Rmax0.4-Rmax64 or Rz0.025-Rz1.6.

3. The chamber structure of claim 1, wherein the at least one cylindrical chamber further comprises a turbulent flow section; the turbulent flow section is provided with a curved wall which is recessed in a direction away from the piston working section, and the curved wall is connected to the side wall of the piston working section.

4. The chamber structure of claim 3, wherein the barrel is further provided with an outlet channel and an inlet channel which are in communication with the at least one cylindrical chamber; and an axis of the outlet channel and an axis of the inlet channel are offset from the axis of the piston working section.

5. The chamber structure of claim 4, wherein a distance between an axis of the outlet channel and the axis of the piston working section is 0.1 mm-50 mm; a distance between an axis of the inlet channel and the axis of the piston working section is 0.1 mm-50 mm;
   and two ends of the outlet channel and two ends of the inlet channel are respectively provided with a fillet having a radius of 0.05 mm-1.5 mm.

6. The chamber structure of claim 3, wherein the curved wall and the side wall of the piston working section are connected by a tool withdrawal groove, and a width of the tool withdrawal groove is 0.1 mm-10 mm.

7. The chamber structure of claim 1, wherein the at least one cylindrical chamber further comprises a clearance section with an inner diameter larger than that of the piston working section; the clearance section is connected to the second end of the first arc section; a side wall of the clearance section is provided with an annular groove; and a blocking piece is embedded in the annular groove.

8. The chamber structure of claim 1, wherein the at least one cylindrical chamber further comprises a guide section, and one end of a side wall of the guide section is connected to the joint section.

9. The chamber structure of claim 8, wherein the guide section comprises a linear section and a second arc section; two ends of the second arc section are respectively connected to the linear section and the second end of the first arc section; the linear section is parallel to the axis of the piston working section; a first end of the second arc section is tangent to the second end of the first arc section; and a second end of the second arc section is tangent to the linear section.

10. The chamber structure of claim 8, wherein the guide section comprises an inclined section, a third arc section, and a linear section; the second end of the first arc section, the inclined section, the third arc section and the linear section are connected in sequence; the linear section is parallel to the axis of the piston working section; the first arc section is tangent to the inclined section; the inclined section is tangent to the third arc section; and the third arc section is tangent to the linear section.

11. The chamber structure of claim 8, wherein the at least one cylindrical chamber further comprises a clearance section with an inner diameter larger than that of the piston working section; two ends of the guide section are respectively connected to the joint section and the clearance section; the side wall of the clearance section is provided with an annular groove; and a blocking piece is embedded in the annular groove.

12. The chamber structure of claim 1, wherein the at least one cylindrical chamber consists of at least two cylindrical chambers.

13. A medical plunger pump comprising the chamber structure of claim 1, wherein a piston assembly is slidably provided in the cylindrical chamber; the piston assembly comprises the push rod and a piston; and the piston comprises a sealing portion tightly attached to a side wall of the piston working section and a joint portion that is able to engage with the push rod in the joint section.

14. The medical plunger pump of claim 13, wherein the joint portion comprises at least two claws; one end of each of the at least two claws is connected to the sealing portion, and the other end of each of the at least two claws is extendable in a direction deviating from an axis of the sealing portion; and a clamping cavity is formed after the at least two claws are closed; and
   a clamping portion is provided at one end of the push rod to cooperate with the at least two claws in the joint section in a snap fit.

* * * * *